(12) United States Patent
Dunn et al.

(10) Patent No.: US 12,156,024 B2
(45) Date of Patent: Nov. 26, 2024

(54) TRANSPARENT SECURE LINK FOR POINT-OF-CARE DEVICES

(71) Applicant: Laboratory Corporation of America Holdings, Burlington, NC (US)

(72) Inventors: Edward Dunn, Burlington (CA); Gordon Lo, Milton (CA)

(73) Assignee: Laboratory Corporation of America Holdings, Burlington, NC (US)

( * ) Notice: Subject to any disclaimer, the term of this patent is extended or adjusted under 35 U.S.C. 154(b) by 388 days.

(21) Appl. No.: 17/243,655

(22) Filed: Apr. 29, 2021

(65) Prior Publication Data
US 2021/0345103 A1 Nov. 4, 2021

Related U.S. Application Data

(60) Provisional application No. 63/018,334, filed on Apr. 30, 2020.

(51) Int. Cl.
*H04L 29/06* (2006.01)
*H04W 12/037* (2021.01)

(52) U.S. Cl.
CPC ................................ *H04W 12/037* (2021.01)

(58) Field of Classification Search
CPC .... H04W 12/037; H04W 12/03; G16H 10/60; G16H 10/40; G16H 15/00; G16H 40/67; G16H 80/00; H04L 63/04
(Continued)

(56) References Cited

U.S. PATENT DOCUMENTS

| 7,912,733 B2 * | 3/2011 | Clements ............... G16H 80/00 705/2 |
| 2003/0154110 A1 * | 8/2003 | Walter ................... G16H 40/20 705/3 |

(Continued)

FOREIGN PATENT DOCUMENTS

| AU | 2016200158 A1 | 8/2016 |
| CN | 104462854 A * | 3/2015 |

(Continued)

OTHER PUBLICATIONS

Kost, G. et al., "The Laboratory-Clinical Interface, Point-of-Care Testing," Chest 115:1140-1154 (1999).
(Continued)

*Primary Examiner* — Longbit Chai
(74) *Attorney, Agent, or Firm* — Kilpatrick Townsend & Stockton LLP (57) ABSTRACT

Aspects and features relate to a system that transparently connects point-of-care testing (POCT) devices with electronic health records associated with a remote laboratory information system (LIS) to report test results in real time or near real time. POCT results can be received from the POCT device at a mobile computing device. The mobile computing device and the POCT device are located outside the LIS environment, for example, at a physician office or remote clinic. The mobile computing device can use its own data broker to configure low-level instrument protocol data from the POCT device for secured transmission over a wide-area network infrastructure. The POCT results can be subsequently received in the LIS environment and provided to the LIS to transparently populate an electronic medical record (EMR) with the POCT results. In some examples, the LIS or a hospital information system can also update a point-of-care EMR.

16 Claims, 10 Drawing Sheets

(58) Field of Classification Search
USPC .......................................................... 726/26
See application file for complete search history.

(56) References Cited

U.S. PATENT DOCUMENTS

| | | | | |
|---|---|---|---|---|
| 2005/0132214 A1* | 6/2005 | Naftali | .................... | H04L 69/16 |
| | | | | 726/26 |
| 2006/0130123 A1* | 6/2006 | Andreev | ............ | H04L 63/0281 |
| | | | | 713/153 |
| 2009/0175165 A1* | 7/2009 | Leighton | ............ | H04L 61/2575 |
| | | | | 370/221 |
| 2012/0232367 A1* | 9/2012 | Allegri | ................... | G16H 40/20 |
| | | | | 600/365 |
| 2012/0233679 A1* | 9/2012 | Shedrinsky | ............ | A61B 5/002 |
| | | | | 726/7 |
| 2012/0324093 A1* | 12/2012 | He | ...................... | G06F 11/3093 |
| | | | | 709/224 |
| 2016/0180022 A1* | 6/2016 | Paixao | ................ | H04L 63/1408 |
| | | | | 705/3 |
| 2017/0006141 A1* | 1/2017 | Bhadra | ................... | H04W 4/70 |
| 2017/0374057 A1* | 12/2017 | Petrovichev | ........ | H04L 63/0823 |
| 2019/0392929 A1* | 12/2019 | Gassman | ............... | G16H 40/63 |
| 2021/0304878 A1* | 9/2021 | Padmani | ................. | H04L 67/55 |

FOREIGN PATENT DOCUMENTS

| | | | | |
|---|---|---|---|---|
| WO | 2016048619 A1 | 3/2016 | | |
| WO | WO-2021191093 A1 * | 9/2021 | ............. | G16H 10/60 |

OTHER PUBLICATIONS

CA3176767, "Office Action", Apr. 11, 2024, 7 pages.
PCT/US2021/029779, "International Preliminary Report on Patentability", Nov. 10, 2022, 8 pages.

\* cited by examiner

TRANSPARENT SECURE LINK FOR POINT-OF-CARE DEVICES

CROSS-REFERENCE TO RELATED APPLICATION

Pursuant to 35 U.S.C. § 119, this application claims priority to and filing benefit of U.S. Provisional Application No. 63/018,334 filed Apr. 30, 2020, which is incorporated herein by reference in its entirety for all purposes.

TECHNICAL FIELD

This disclosure generally relates to systems and methods for point-of-care services for medical patients. More specifically, but not by way of limitation, this disclosure pertains to systems and methods to provide point-of-care testing (POCT) and medical record management with an infrastructure that includes high data security while linking remote point-of-care devices to healthcare records in real time or near real time.

BACKGROUND

Although testing of patient specimens at a centralized laboratory is effective for most clinical needs, in certain situations, patients and physicians can benefit from having a test result delivered during the clinical visit. For example, a patient can benefit from on-the-spot clinical advice and further action if the result of an international normalized ratio/prothrombin time (INR/PT) test for blood clotting time can be provided while a patient being monitored during anticoagulant administration is visiting the healthcare provider. The provision of such test results can be achieved through near-patient testing, referred to as "point-of-care testing" (POCT).

A POCT program can enable timely clinical decision making and improves patient engagement while also providing accurate results. POCT continues to expand, driven by new technologies and changes in healthcare delivery models toward patient-focused, community-based healthcare. Results from POCT can be observed and evaluated by a healthcare provider "on the spot" and subsequently entered into medical records by office personnel for future reference. As POCT expands, more and more healthcare providers are learning how to effectively use POCT carried out in their own clinics, as opposed to making use of results based on the same tests carried out on specimens collected by a healthcare provider and shipped to the centralized testing laboratory.

SUMMARY

In one example, a non-transitory computer-readable medium includes computer program code executable by a processor to cause a mobile computing device to receive low-level instrument protocol data from a POCT device located external to a laboratory information system (LIS) environment and configure the low-level instrument protocol data using a data broker on the mobile computing device to produce secured POCT data. The computer program code is further executable by the processor to cause the mobile computing device to transmit the secured POCT data to the LIS environment using a wide-area network infrastructure.

In another example, a system includes a non-transitory computer-readable medium including computer program code to provide a transparent secure link for POCT devices and a processor device communicatively coupled to the non-transitory computer-readable medium. The processor device is configured for executing the computer program code to access low-level instrument protocol data from a POCT device using a mobile computing device. The mobile computing device and the POCT device can be located external to an LIS environment. The processor device is further configured for executing the computer program code to configure the low-level instrument protocol data using a data broker on the mobile computing device to produce secured POCT data, and to transmit the secured POCT data to the LIS environment using a wide-area network infrastructure. A processing device is further configured to execute computer program code to access the low-level instrument protocol data from the secured POCT data in one or both of the wide-area network infrastructure or the LIS environment, and to populate an electronic medical record (EMR) in an LIS of the LIS environment using information from the low-level instrument protocol data accessed from the secured POCT data.

In another example, a method includes accessing low-level instrument protocol data from a POCT device using a mobile computing device, the mobile computing device and the POCT device being located external to an LIS environment. The method also includes configuring the low-level instrument protocol data using a data broker on the mobile computing device to produce secured POCT data and transmitting the secured POCT data to the LIS environment using a wide-area network infrastructure. The method further includes accessing the low-level instrument protocol data from the secured POCT data in at least one of the wide-area network infrastructure or the LIS environment and populating an EMR in an LIS of the LIS environment using information from the low-level instrument protocol data.

In another example, a system includes a non-transitory computer-readable medium including computer program code and a processor device communicatively coupled to the non-transitory computer-readable medium. The processor device is configured for executing the computer program code to access low-level EMR data within a laboratory information system (LIS) environment or a hospital information system (HIS) environment and configure the low-level EMR data using a remote broker to produce secured EMR data. The processor device is further configured to transmit the secured EMR data to a point-of-care (POC) environment using a wide-area network infrastructure. The low-level EMR data is accessed from the secured EMR data in the POC environment, with the POC environment being outside of the LIS or HIS environment. The POC EMR is updated using information from the low-level EMR data accessed from the secured EMR data.

DETAILED DESCRIPTION

Aspects and features of this disclosure provide a system that can transparently connect remote point-of-care test (POCT) devices with electronic health records associated with a laboratory information system (LIS) as well as update point-of-care medical records with information from the LIS or a hospital information system (HIS). The system can report test results in real time. The test results can appear substantially as they would if performed in a centralized laboratory associated with the LIS. Additionally, the test results are secured for transmission to the LIS without processing overhead that would otherwise be required for an end-to-end encryption-based solution such as a virtual private network (VPN).

Modern healthcare increasingly relies on the availability of a centralized, electronic medical record (EMR) for each patient. A centralized EMR can be securely accessed by multiple providers such as hospitals, clinics, and physician offices. A patient's EMR can be kept up to date so that each provider has access to crucial medial history without having to collect it from the patient each time a medical service is provided. Test results are typically provided as part of a patient's EMR. When a test is carried out on a specimen collected by a healthcare provider and shipped to a centralized testing laboratory, the test result(s) can be input to a copy of the EMR stored in the laboratory's centralized LIS. The EMR is then automatically updated everywhere it resides and can be accessed by the patient's healthcare provider(s), including the one that collected the specimen and requested the test.

POCT devices have been unable to connect to centralized electronic medical systems in a manner which allows a patient's electronic medical record (EMR) to be updated in real time or near real time with test results obtained using a POCT device. In some cases, test results obtained from the device itself are eventually entered into the patient's EMR by the healthcare provider. In other cases, the POCT device may transfer test results to a proprietary system maintained by the manufacturer of the POCT device for access by the healthcare provider. The healthcare provider may eventually enter the results into the patient's EMR. In either case, the availability of test results to other providers is delayed and test results may not be recorded at all, or may not be accurately entered into patient records.

Aspects and features of the system herein include network communication between a POCT device external to the LIS environment and the LIS in order to enable a secured, automatic, real-time transfer of POCT results to the LIS, and ultimately to a patient's EMR. In addition, the test results are provided to the EMR automatically and transparently, meaning that the test results can be quickly and automatically formatted for display as part of the EMR in the same manner as similar test results obtained through traditional, centralized laboratory testing, thus eliminating the need for manual transcription and/or interpretation. This enables healthcare professionals to complete laboratory testing at an external location and at a time that is convenient to the healthcare provider and to the patient while automatically populating the patient's EMR with the test results, improving the timeliness and accessibility of laboratory test results from POCT devices. An LIS or an HIS can also populate a point-of-care EMR with test results or other information. For purposes of this disclosure, an LIS and an HIS are interchangeable and either can include EMRs and receive and/or transmit test result data or EMR data as described herein.

In some examples, a system includes a wireless, mobile computing device (e.g. tablet or smartphone) with computer program code to establish a connection to a POCT device located proximate to the mobile computing device. Both the POCT device and the computing device can be located external to the LIS environment. The computer program code causes the mobile computing device to receive POCT results in the form of low-level instrument protocol data, produce secured POCT data, and transmit the secured POCT data including the test results to a remote LIS. The system can make use of centralized middleware to transparently populate an EMR associated with the LIS with the POCT results.

In some examples, the secured POCT result data is produced using a data broker on the mobile computing device and is provided to a remote broker over a wide-area network infrastructure that may include the Internet, and then provided to the LIS. In some examples, the POCT results are provided to centralized middleware configured to format the POCT result data for the EMR. Test results can be made available as part of the patient's EMR in real time or near real time. For example, an EMR update including the test results can be transmitted back to the mobile computing device that interfaced with the POCT device, or to another computing device at a healthcare provider office so that the test results can quickly be viewed as part of the patient's EMR.

In some examples, a system includes the capability to access low-level EMR data within an LIS or HIS environment and configure the low-level EMR data using a remote broker to produce secured EMR data. The low-level EMR data can be transmitted to a point-of-care (POC) environment using a wide-area network infrastructure. The low-level EMR data is accessed from the secured EMR data in the POC environment. The POC environment is outside of the LIS or HIS environment. The low-level EMR data can then be used to populate or update a POC EMR.

Detailed descriptions of certain examples are discussed below. These illustrative examples are given to introduce the reader to the general subject matter discussed here and are not intended to limit the scope of the disclosed concepts. The following sections describe various additional aspects and examples with reference to the drawings in which like numerals indicate like elements, and directional descriptions are used to describe the illustrative examples but, like the illustrative examples, should not be used to limit the present disclosure.

Figure 1:
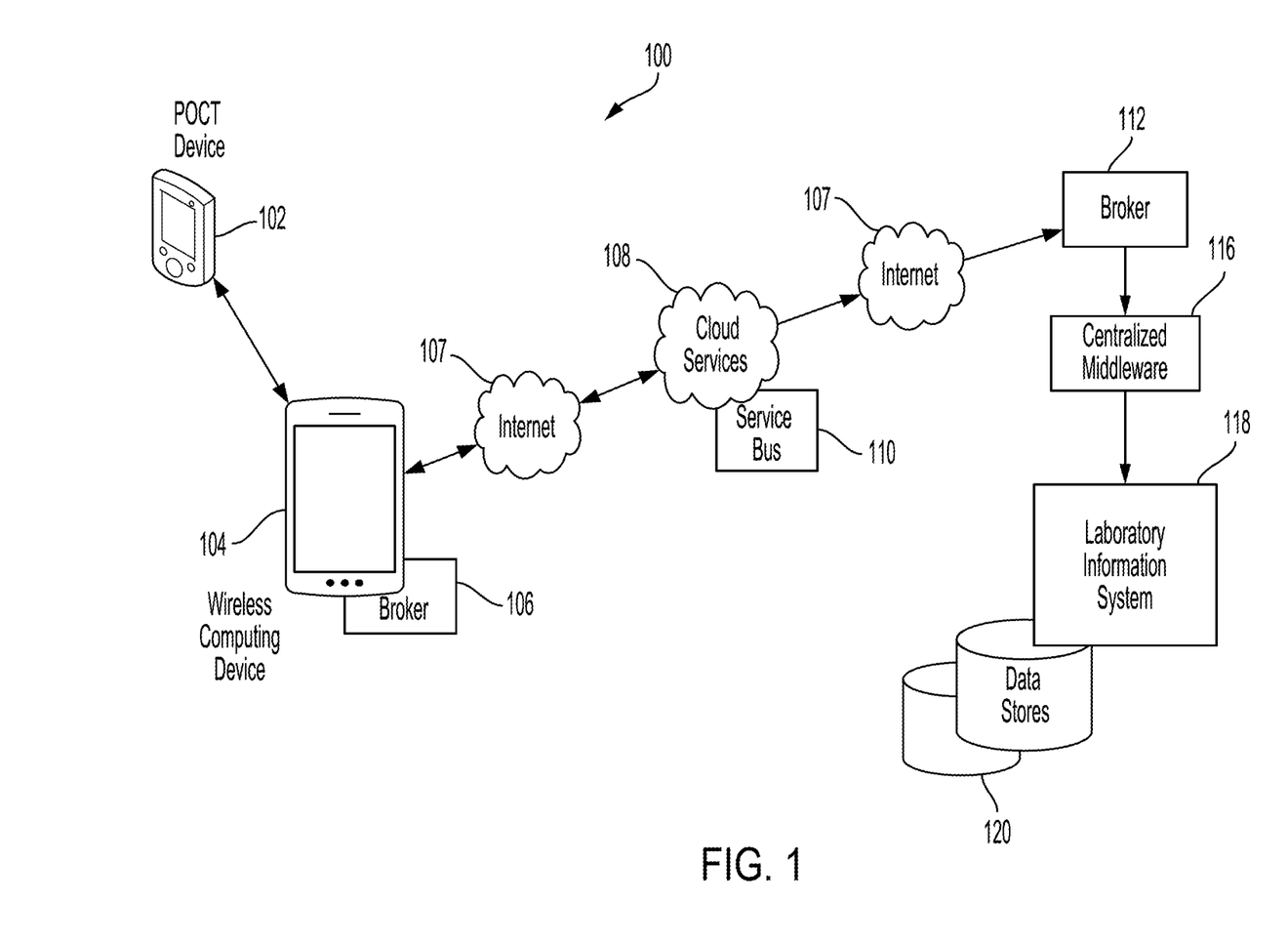
FIG. 1 is a block diagram depicting a system for providing a transparent secure link for point-of-care testing (POCT) devices according to aspects of the present disclosure.

Referring now to the drawings, FIG. 1 depicts an example of a system 100 for providing a transparent secure link for POCT devices according to aspects of the present disclosure. System 100 includes POCT device 102 and mobile, wireless computing device 104. Both the POCT device and the mobile computing device are located external to the LIS environment, for example, at a healthcare provider office or at a remote clinic. Computing device 104, as an example, can be a tablet computer or mobile phone. Alternatively, computing device 104 can be a laptop or notebook computer. As another alternative, a desktop workstation can be used as a mobile computing device. POCT device 102 interfaces with mobile computing device 104 via a wireless connection, for example, Bluetooth, Wi-Fi, NFC, etc. In one example, mobile computing device 104 activates a Wi-Fi hotspot through which POCT device 102 can be accessed with computer program code on mobile computing device 104, for example, an application or "app." The wireless, mobile computing device also includes local data broker 106, which may be part of the application or a separate software module expressly for transmitting POCT result data to remote systems over a wide-area network infrastructure that in this example includes the Internet 107 and a cloud services platform 108.

Local data broker 106 can be a message oriented middleware software module to handle the flow of data between the POCT device 102 and service bus 110 deployed in the cloud services platform 108. Local data broker 106 serves as an intermediary for the application that handles POCT on the mobile computing device 104, and other applications to which the mobile computing device must interface over the wide-area network infrastructure. Service bus 110 is used to decouple the application on the mobile computing device 104 from applications deployed in or behind the wide-area network infrastructure. The service bus 110 also provides load-balancing, routing, and control access and may include cloud service message queues such as an incoming message queue and a POCT queue. Local data broker 106 translates and/or encapsulates low-level instrument protocol data received from POCT device 102 to provide secured POCT data to traverse the wide-area network infrastructure without the need for an end-to-end encrypted channel such as might otherwise be provided by a VPN connection.

Still referring to FIG. 1, remote broker 112 receives secured POCT data over the wide-area network infrastructure from local data broker 106. In this example, remote broker 112 handles the flow of data between local data broker 106 and centralized middleware 116. Remote broker 112 access the low-level instrument protocol data, or at least information from the low-level instrument protocol data, from the secured POCT data in order to populate an EMR in the laboratory information system 118 with test results. In this example, centralized middleware 116 provides a translation layer between remote broker 112 and LIS 118. Centralized middleware 116 includes stored information regarding the data elements in low-level instrument protocol data and the data elements maintained in the LIS for patient EMRs. Centralized middleware 116 formats information from the low-level instrument protocol data received from remote broker 112 for storage in the LIS 118 as part of an EMR by mapping data elements from one to the other as appropriate.

LIS 118 includes one or more servers, each with a processor or processors and computer program code instructions for causing the processor or processors to operate the LIS 118. LIS 118 includes various data stores 120. These data stores may include, as examples, a laboratory management data store, a healthcare provider data store, a health plan provider data store, and a laboratory data store. Medical code databases and policy databases may also be included. A laboratory information database may contain information distinguishing internal laboratories from external laboratories and from POCT testing locations.

Data stores 120 and LIS 118 are part of an LIS environment. The LIS environment also includes instruments and computer systems (not shown), if any, within testing laboratories, hospitals, clinics, etc. that are connected to the LIS via LAN, virtual LAN, VPN, or are otherwise within the firewall or information security structure of the LIS. A device that is not connected to or related to the LIS in any of these ways can be said to be outside of or external to the LIS environment. Laboratories, hospitals, clinics, and the like are that are inside the LIS environment are typically affiliated or partnered in some way with the same entity that maintains the LIS. Remote data broker 112 and centralized middleware 116 may be part of the LIS environment, part of the wide-area network infrastructure, or components of either or both can reside in both.

Figure 2:
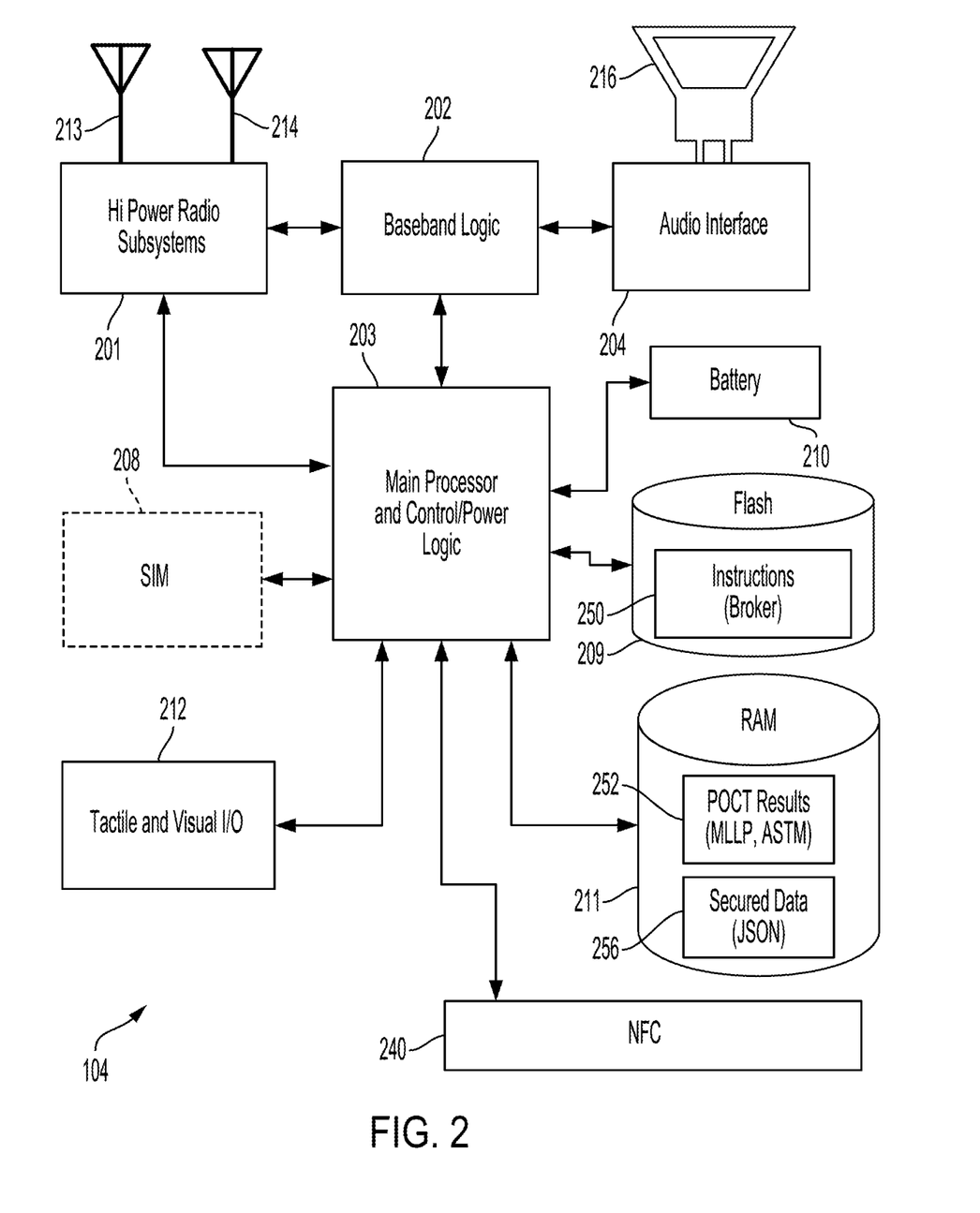
FIG. 2 is a is a block diagram depicting a device for providing a transparent secure link for a POCT device according to aspects of the present disclosure.

FIG. 2 is a is a block diagram depicting a mobile computing device for providing a transparent secure link for a POCT device according to aspects of the present disclosure. Referring now to FIG. 2, the exemplary wireless, mobile computing device 104 from FIG. 1, for example, a tablet computer, will be described detail. The mobile computing device of FIG. 2 includes a high power radio subsystems block 201, a baseband logic block 202, a main processor and control logic block ("main logic") 203, and an audio interface block 204. A subscriber identity module (SIM) 208 is shown as operatively connected to the main processor and control logic. The SIM is used to connect to a cellular network, and is optional. The SIM, if present, may be a discrete device or electronic (an eSIM). The SIM can include subscriber information to allow the computing device 104 to connect to the wide-area network infrastructure using LTE or another cellular protocol. The SIM may also be present and not activated if it is not needed for a particular device because the device is always in range of a Wi-Fi connection to the Internet.

Also included in mobile computing device 104 is flash storage 209, a battery 210, and random access memory (RAM) 211. The RAM 211 may include various memory devices and possibly memory dedicated to specific purposes such as graphics. A portion of RAM 211 may be used to store the data currently being viewed on the display of the mobile computing device. The display (not shown) is part of tactile and visual input/output (I/O) block 212. Within the high power radio subsystems block 201, the transmit and receive information is converted to and from the radio frequencies (RF) of the various carrier types, and filtering using baseband or intermediate frequency circuitry is applied. Radio subsystems for local communication such as for Wi-Fi and Bluetooth are included in this block. The device's main antenna system 213 is connected to the radio subsystems block 201. The device also includes a combination Wi-Fi/Bluetooth antenna 214. Mobile computing device 104 also includes a bi-directional, short-range near-field communication (NFC) interface 240.

Still referring to FIG. 2, the audio interface block 204 handles voice as well as analog-to-digital (A/D) and D/A processing. It also produces output through speaker 216, which may include acoustic signaling to notify a clinician of a connection being established with POCT device 102, or POCT results being received from POCT device 102, etc. In the baseband logic block 202, basic signal processing occurs, e.g., synchronization, channel coding, decoding and burst formatting. The main logic 203 coordinates the aforementioned blocks and also plays a role in controlling the interface components such as a screen and touch interface or keyboard. The functions of the aforementioned blocks are directed and controlled by a processor or processor devices included in the main logic, such as general-purpose microprocessors, digital signal processors (DSPs), application specific integrated circuits (ASICs), various types of signal conditioning circuitry, including analog-to-digital converters, digital-to-analog converters, input/output buffers, etc.

The flash storage 209 shown in FIG. 2 includes one or more memory devices such as at least one array of non-volatile memory cells. RAM 211 includes one or more memory devices such as at least one array of dynamic random access memory (DRAM) cells. The content of the flash memory may be pre-programmed and write protected thereafter, whereas the content of at least portions of the RAM may be selectively modified and/or erased. The flash memory device, therefore, is non-transitory computer-readable medium that is used to store operating system software and application programs (apps), including an app 250, which includes instructions executable by computing device 104 to carry out the transparent, real-time, secure linking of the POCT device 102 to the network and ultimately to the LIS 118. In this example, app 250 includes local data broker 106. RAM may be used to temporarily store POCT results 252 and secured POCT data 256. In some examples, the POCT results take the form of low-level instrument protocol data. For purposes of this example, POCT results can include data according to a low-level instrument protocol such as minimum lower layer protocol (MLLP) or a protocol that follows a standard of the American Society for Testing and Materials (ASTM). Secured POCT data is the test result data encapsulated or otherwise converted by data broker 106 for transmission over the wide-area network infrastructure. For example, the test result data can be formatted as transport control protocol (TCP) messages and the messages can be encapsulated as JavaScript object notation (JSON) messages.

Figure 3:
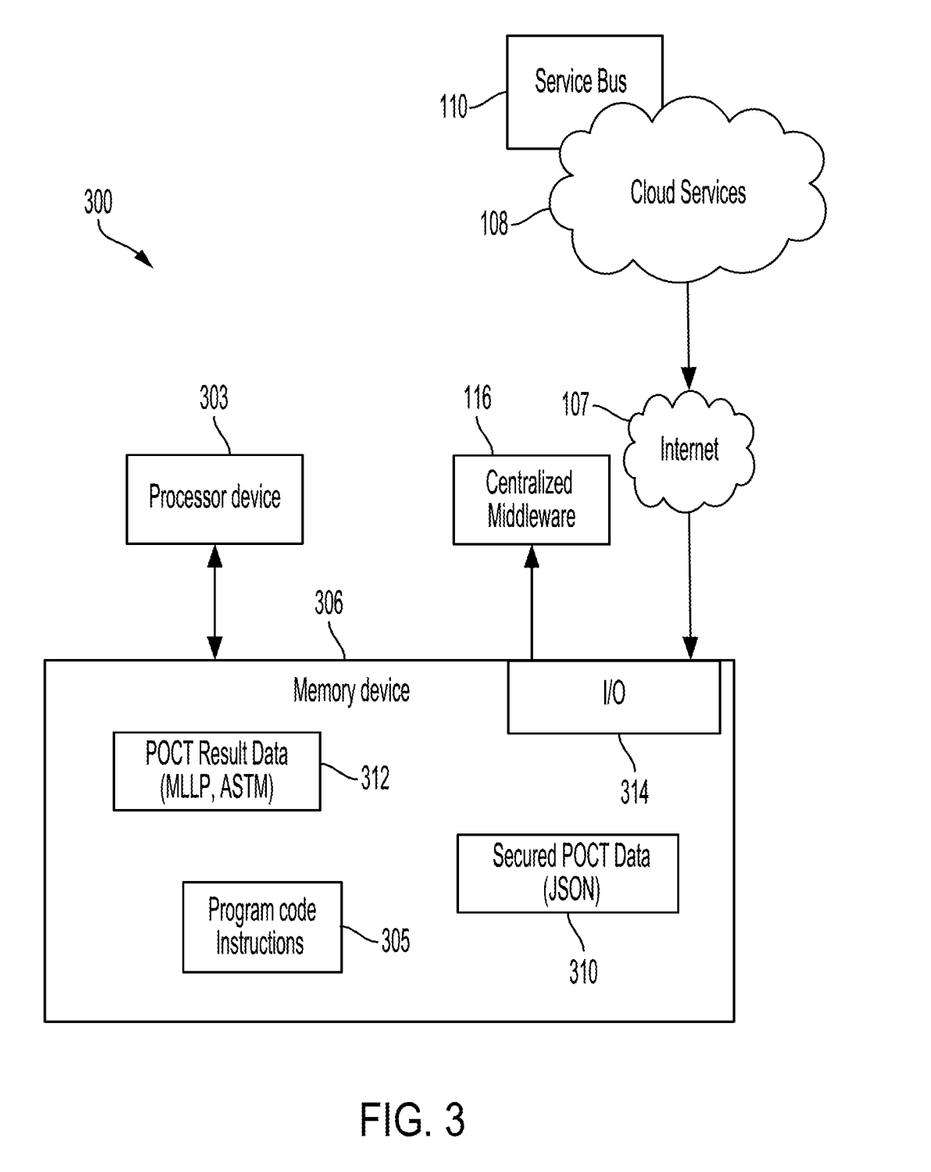
FIG. 3 is a block diagram depicting another system for providing a transparent secure link for POCT devices according to aspects of the present disclosure.

FIG. 3 is a block diagram depicting another system for providing a transparent secure link for POCT devices according to aspects of the present disclosure. The system 300 includes processor device 303 and memory device 306 communicatively coupled to processor device 303. Such a system may implement, as an example, a network server within or connected to the wide-area network infrastructure of FIG. 1, or with the LIS environment. Processor device 303 can execute computer program code, also referred to as instructions or program code instructions 305, for performing operations of remote broker 112 of FIG. 1. The processor device 303 can read the secured POCT data 310 from service bus 110 using the wide-area network infrastructure, temporarily store the secured POCT data 310 in memory device 306, access encapsulated POCT result data by de-encapsulating the data, for example, from JSON messages, and forward the original POCT result data 312 to centralized middleware 116. POCT result data 312 can be temporarily stored in memory device 306. The POCT result data can be the original low-level instrument protocol data from the POCT device or information derived from or describing the low-level instrument protocol data.

Non-limiting examples of the processor device 303 include a field-programmable gate array (FPGA), an application-specific integrated circuit (ASIC), a microprocessor, etc. The processor device 303 can execute one or more operations for running program code instructions 305 stored in the memory device 306. Computer program code instructions 305 can include executable instructions to receive secured POCT data from cloud services platform 108, store secured POCT data 310, access POCT result data 312, store POCT result data 312, and forward POCT result data on centralized middleware 116.

Memory device 306 can include one memory device or multiple memory devices. The memory device 306 can be non-volatile and may include any type of memory device that retains stored information when powered off. In some examples, at least some of the memory device can include a non-transitory computer-readable medium from which the processor device can read instructions 305. A computer-readable medium can include electronic, optical, magnetic, or other storage devices capable of providing the processor device with computer-readable instructions 305 or other program code. Non-limiting examples of the memory device 306 include electrically erasable and programmable read-only memory (EEPROM), flash memory, or any other type of non-volatile memory. Non-limiting examples of a computer-readable medium include magnetic disk(s), memory chip(s), ROM, random-access memory (RAM), an ASIC, a configured processor, optical storage, or any other medium from which a computer processor can read instructions. Memory device 306 also includes an input/output (I/O) module or modules 314, and a bus or interconnect (not shown) to allow for inter- and intra-device communications. I/O module 314 can include a network interface (not shown), which in turn communicates with cloud services platform 108.

Figure 4:
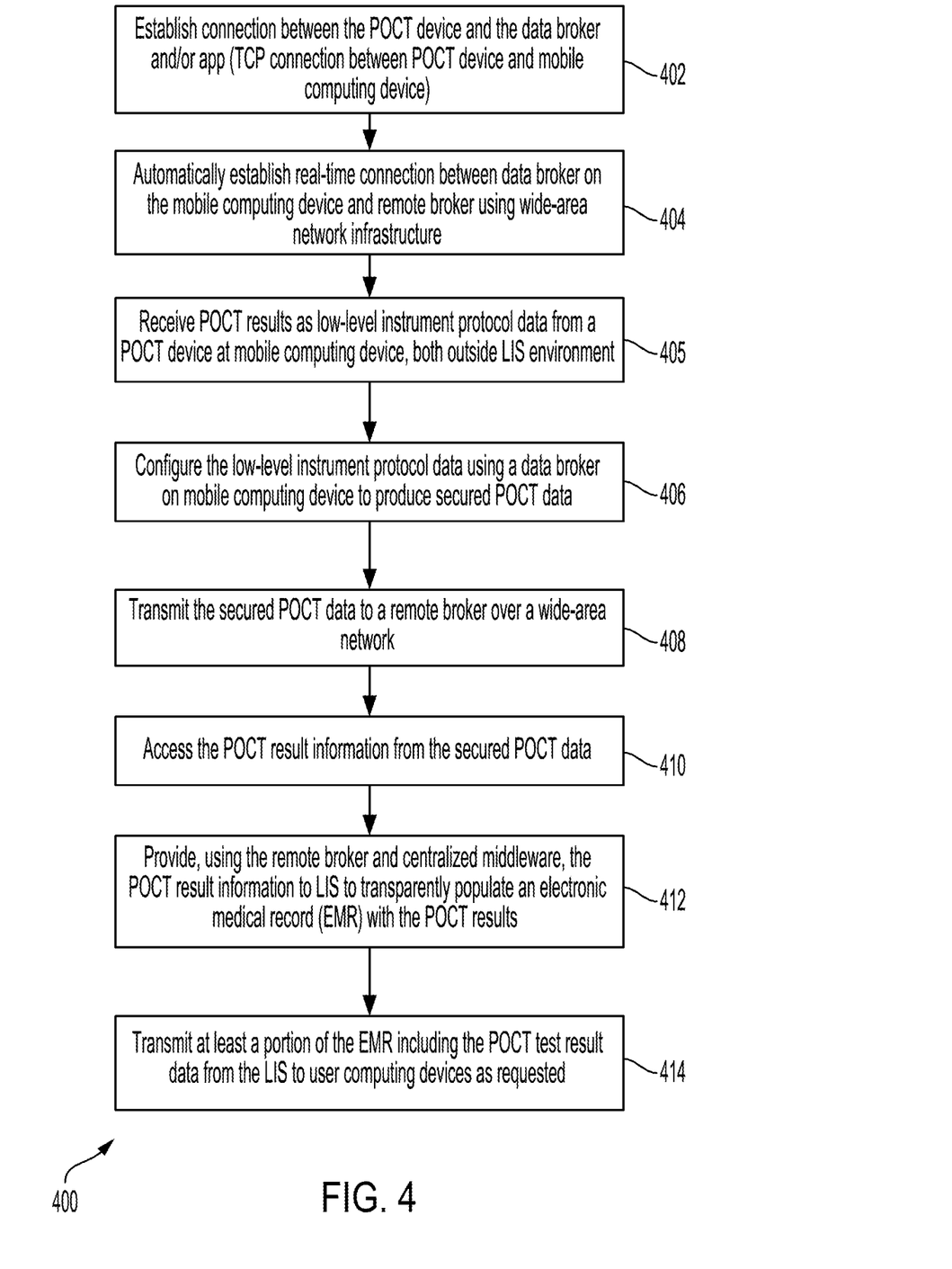
FIG. 4 is a flowchart illustrating a process of providing a transparent secure link for a POCT device according to aspects of the present disclosure.

FIG. 4 is a flowchart illustrating a process of providing a transparent secure link for a POCT device according to aspects of the present disclosure. Process 400 of FIG. 4 is described below with reference to components discussed above. At block 402, the processing device within main logic 203 establishes a connection between the POCT device and the local data broker in the mobile computing device. The POCT device and the mobile computing device are outside the LIS environment. The connection includes a TCP connection between the POCT device and the mobile computing device. At block 404, a real-time connection is automatically established between the local data broker and the remote broker in response to the connection of the POCT device. The real-time connection between the broker in an application on the mobile computing device and the downstream, remote broker provides a real-time connection between the POCT device and the LIS 118. At block 405, the processing device within main logic 203 receives POCT results 252 from the point-of-care testing device 102. The POCT results, as an example, are received as low-level instrument protocol data. At block 406, the processing device within control logic 203 configures the low-level instrument protocol data using the local data broker to produce secured POCT data 256 for transit to the LIS 118. In one example, the processor device configures the POCT test result data by encapsulating low-level (TCP) messages containing the test result data within JSON messages. At block 408, the secured POCT data is transmitted to the remote broker over a wide area network infrastructure including cloud services platform 108.

At block 410, processor device 303 causes the remote broker to access the POCT result data from the secured POCT data 310, for example, by de-encapsulating the low-level instrument protocol data from the JSON messages. At block 412, processor device 303 can provide the POCT results 312 to the LIS 118 to populate an EMR. The POCT results may be provided to centralized middleware 116 for additional formatting and data matching in order to transparently populate the EMR with the test result(s). Once the EMR is populated with the test results, the EMR or a portion of the EMR including the POCT results can be accessed from the LIS by provider computing devices as requested. When requested, the EMR can be transmitted at block 414 to the provider computing device. In some examples, the provider computing device is any computing device used by a clinician, physician, or similar healthcare provider to access the patient's records. A point-of-care EMR, such as an EMR maintained by a physician office, can also be updated from the LIS to include test results or other information as described below with respect to FIGS. 10 and 11.

Figure 5:
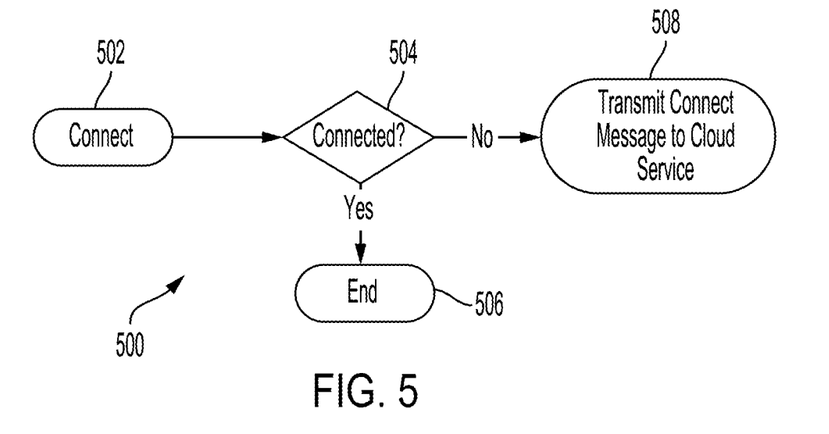
FIGS. 5-8 are additional flowcharts illustrating processes for providing a transparent secure link for a POCT device according to aspects of the present disclosure.
Figure 6:
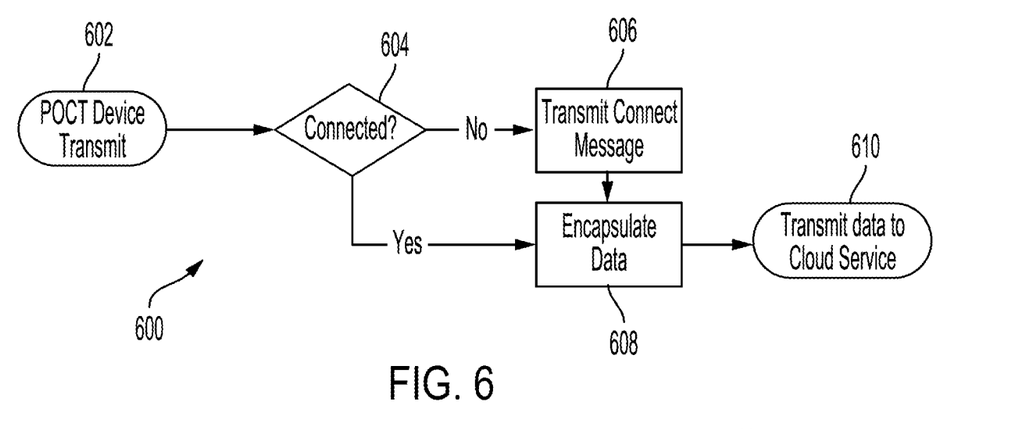
Figure 7:
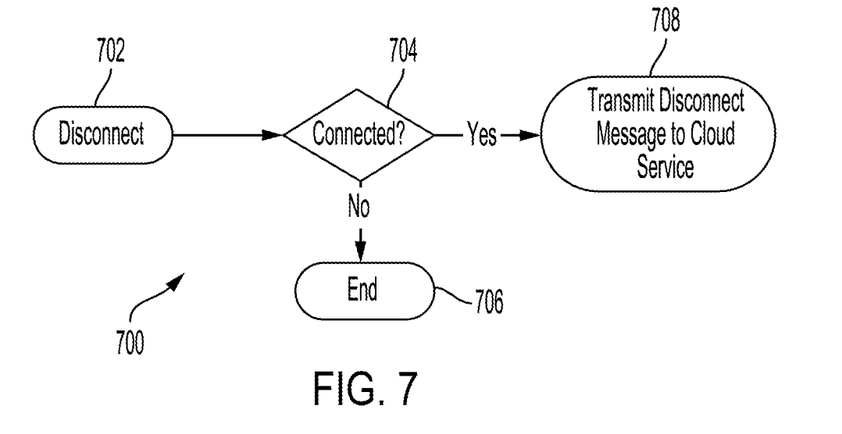

FIGS. 5-7 are flowcharts illustrating processes used in providing a transparent secure link for a POCT device according to aspects of the present disclosure. These figures illustrate how the mobile computing device application interacts with the cloud services platform. FIG. 5 illustrates connection process 500. At block 502 the POCT device connects to the mobile computing device, and the mobile computing device determines at block 504 if it is already connected to the appropriate cloud service. If so, the process ends at block 506 otherwise, the mobile computing device application sends a connect message to the cloud service at block 508. The mobile computing device may connect with one cloud service or multiple cloud services. As examples, cloud services may include a coding/decoding service, additional middleware, additional brokers, and/or message queues. In this example, on POCT TCP connect, the connect messaging of FIG. 5 and FIG. 6 causes the establishment of a Web socket connection to service bus 110 to listen for messages and establishes a Web socket connection to service bus 110 to send messages.

FIG. 6 illustrates an example of transmitting data. When data is transmitted from the POCT device at block 602 of process 600, a connected status for the system is determined at block 604. If the system is not connected, either because a connect process has not been carried out, or the connection has been lost, a new connect message is generated and transmitted at block 606. Otherwise, data encapsulation takes place at block 608 and the data is transmitted to the appropriate cloud service at block 610. The messages transmitted from the POCT device to the mobile computing device in this example are low-level instrument communication protocols over TCP. When the POCT device sends data to the mobile computing device, the data broker in the mobile computing device can encapsulate the data and submit the data to service bus 110. The mobile computing device application can be designed so that the data broker must send messages and the data is pushed from the POCT device buffer to the application using a TCP:psh,ack command. At the application layer, this command can be interpreted as a message event from the TCP stack.

FIG. 7 illustrates disconnect process 700. At block 702, the POCT device disconnects from the mobile computing device. At block 704, the mobile computing device determines whether an active connection to the system is being maintained. If not, the process ends at block 706. Otherwise, a disconnect messages is transmitted to the cloud services platform 108 at block 708.

Figure 8:
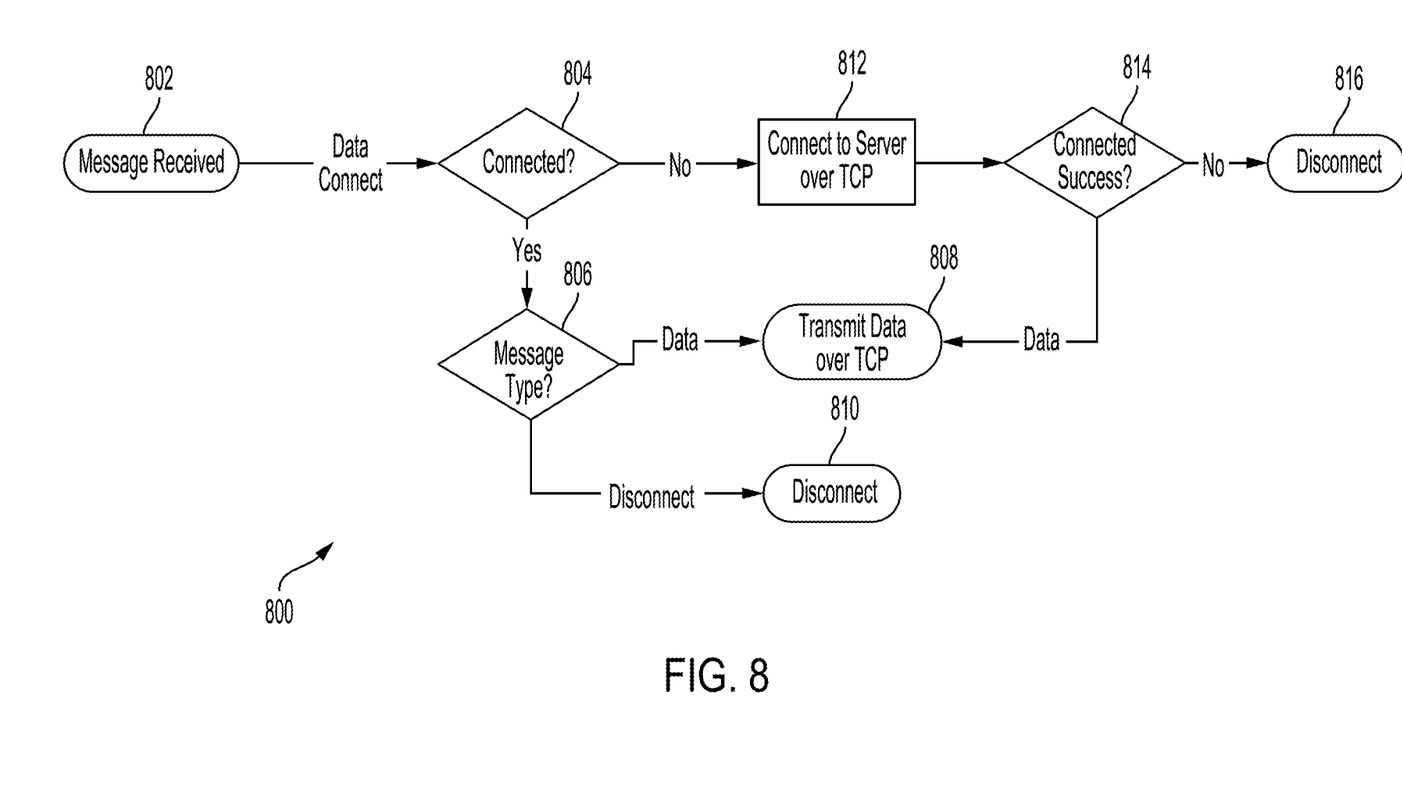

FIG. 8 illustrates an example of a process by which the cloud services platform 108 communicates back to the mobile computing device. At block 802 of process 800, a message is received from an upstream server, for example, one running remote broker 112 and/or centralized middleware 116. A data connection message is transmitted at block 804 to determine if a connection still exists with the application. If so, a determination as to message type is made at block 806. If the message is data, the message is transmitted over TCP at block 808. Otherwise, a disconnect message is transmitted to the mobile computing device at block 810. If the connection does not exist, messaging is transmitted at block 812 in order to reestablish the connection between the POCT device and the upstream platforms. If successful, data is transmitted block 808. Otherwise, a disconnect message is transmitted at block 816.

Figure 9A:
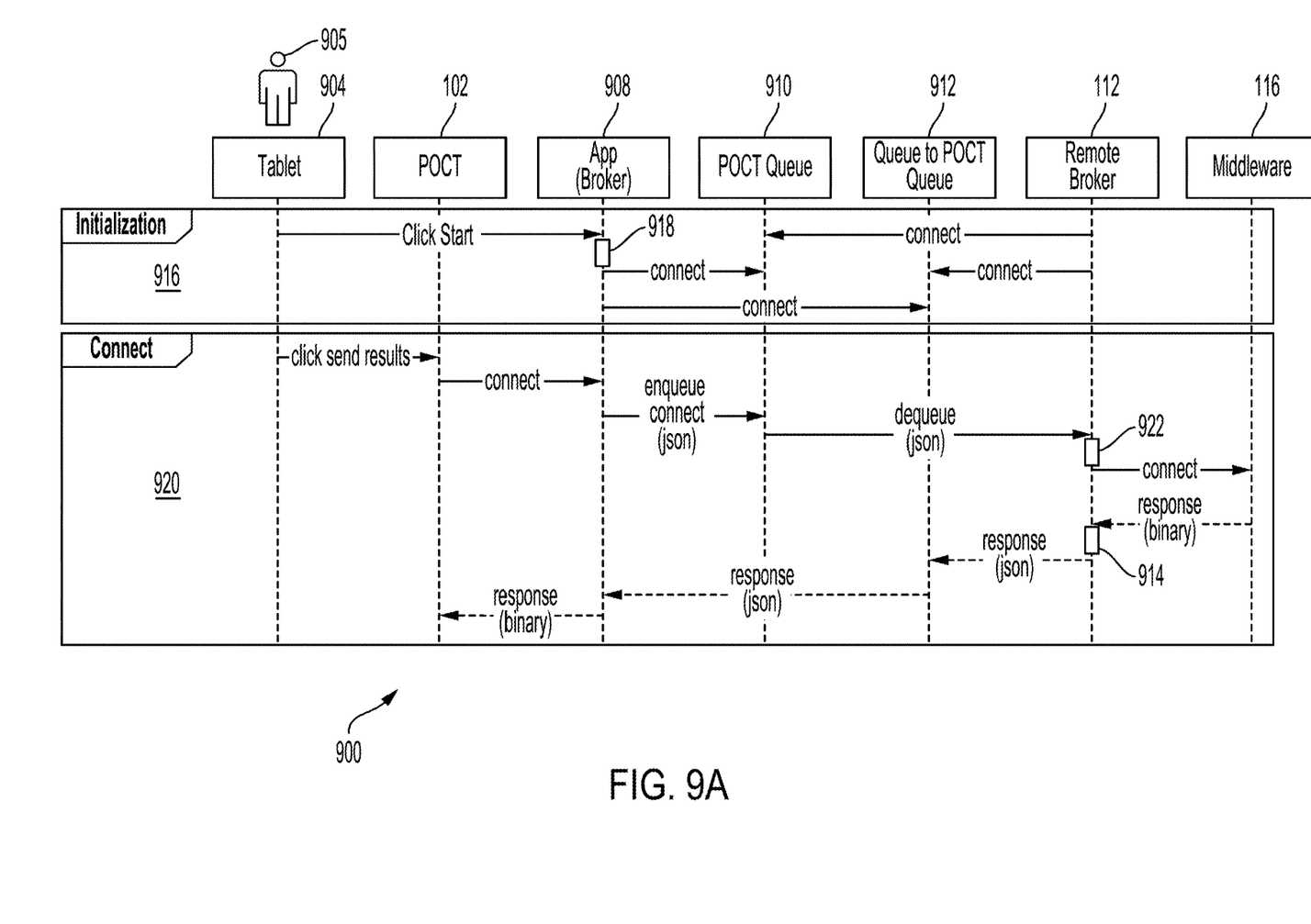
FIG. 9A and FIG. 9B show a message flow diagram of messaging that can be used to provide a transparent secure link for a POCT device according to aspects of the present disclosure.
Figure 9B:
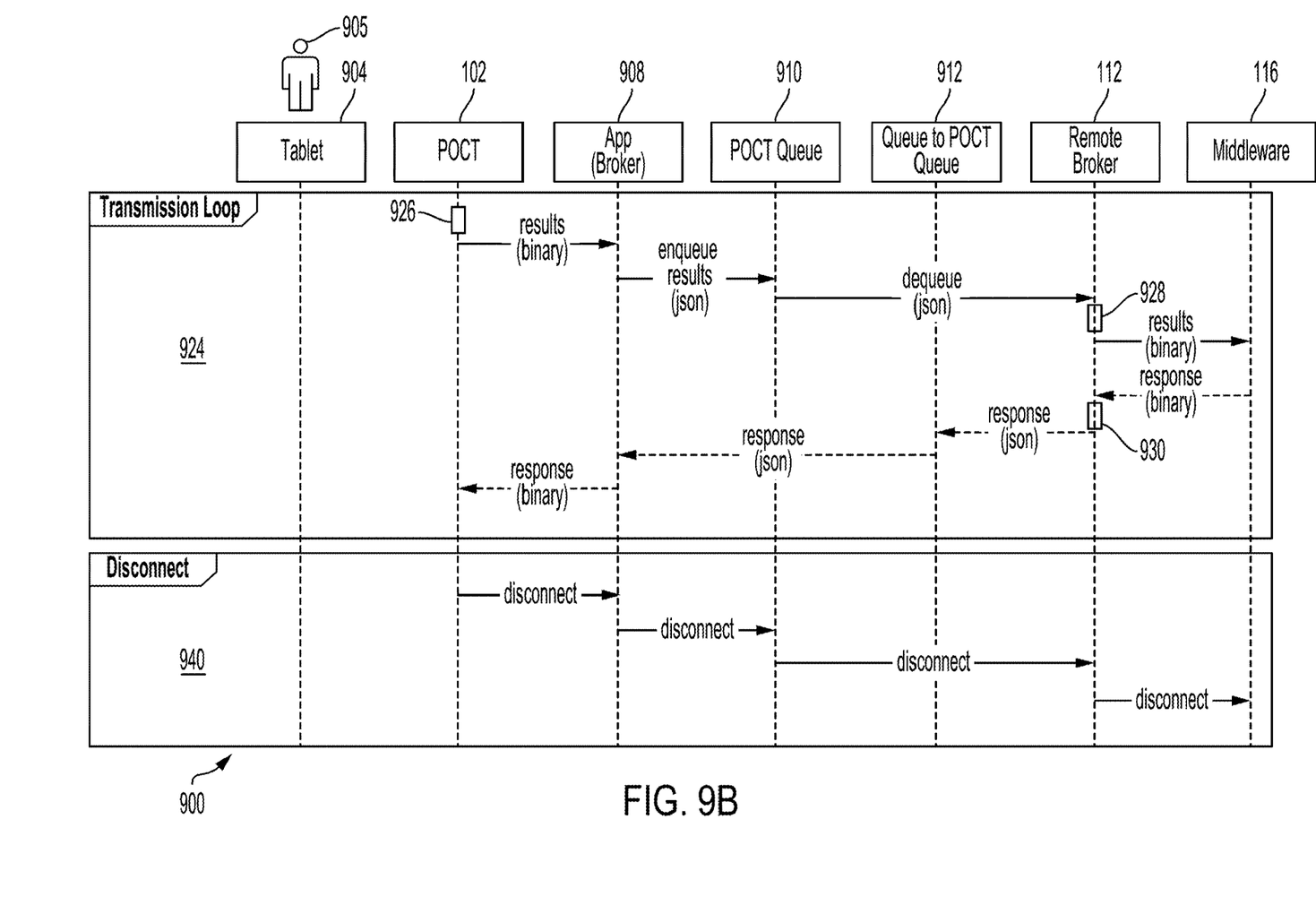

FIG. 9A and FIG. 9B illustrate a message flow 900 that can be used to provide the transparent secure link for a POCT device according to aspects of the present disclosure. In this example, the mobile computing device is a tablet computer 904 being used by healthcare provider personnel 905. POCT device 102 is connecting to tablet computer 904. Tablet computer 902 includes an application 908. That application includes a local data broker as previously discussed. POCT messaging queue 910 is used to exchange data with the POCT device. Messaging queue 912 is used to exchange data with remote broker 112. In this example, remote broker 112 establishes the queue connections automatically and stays connected while POCT is in process. The connection to middleware 116 can also be constant while POCT is in process. Thus, from a user's perspective, the POCT device is maintaining a connection to the remote LIS. Alternatively, connections and disconnections can take place as needed, while still maintaining this user's perspective. Thus, messaging queue 912 exchanges messages with POCT messaging queue 910 and with remote broker 112. Middleware 116, as an example, can be the centralized middleware shown in FIG. 1.

During an initialization phase 916 as shown in FIG. 9A, tablet computer 904 receives an input from healthcare provider personnel to initiate testing. For example, the tablet may receive user input through (I/O) block 212 based on a displayed "Start" or "Begin" virtual button. When application 908 receives this indication, a local TCP port is opened at block 918 to listen for connection messages. The connection messaging illustrated in initialization phase 916 of message flow 900 can then take place. During connection phase 920 of message flow 900, a connection message is sent, enqueued and dequeued, and JSON messages are transmitted through the system. At block 922, a JSON message is de-encapsulated to access the connection request and the connection request is sent to middleware 116 using TCP. The response from the LIS received through middleware 116 is encapsulated into a JSON message at block 914 and the remaining messaging of connection phase 920.

During a transmission loop phase 924 in FIG. 9B, the POCT device acts on the connection response and queues POCT test results accordingly. At block 926, POCT result data is encapsulated in a JSON message to provide secured POCT data that is enqueued and dequeued, and accessed at block 928 to retrieve the original POCT test results. Responses in transmission loop phase 924 proceed in the reverse, with the binary response being encapsulated into a JSON message at block 930. Disconnect phase 940 is entered when testing is complete.

JSON messages shown in the example of FIG. 9 take the format:

```
{
    type: <msg type enum>,
    body: <base64 encoded binary data>
},
``` where the message type is one of "data," "connect," or "disconnect." The body includes raw TCP buffer information that has been base-64 encoded, and is populated only if the message type is "data." As an example, a JSON data transmission message can appear as:

```
{
    type: data,
    body: <aGVsbG93b3JsZA==>
}.
```

An example connect message can appear as:

```
{
    type: connect
}.
```

Figure 10:
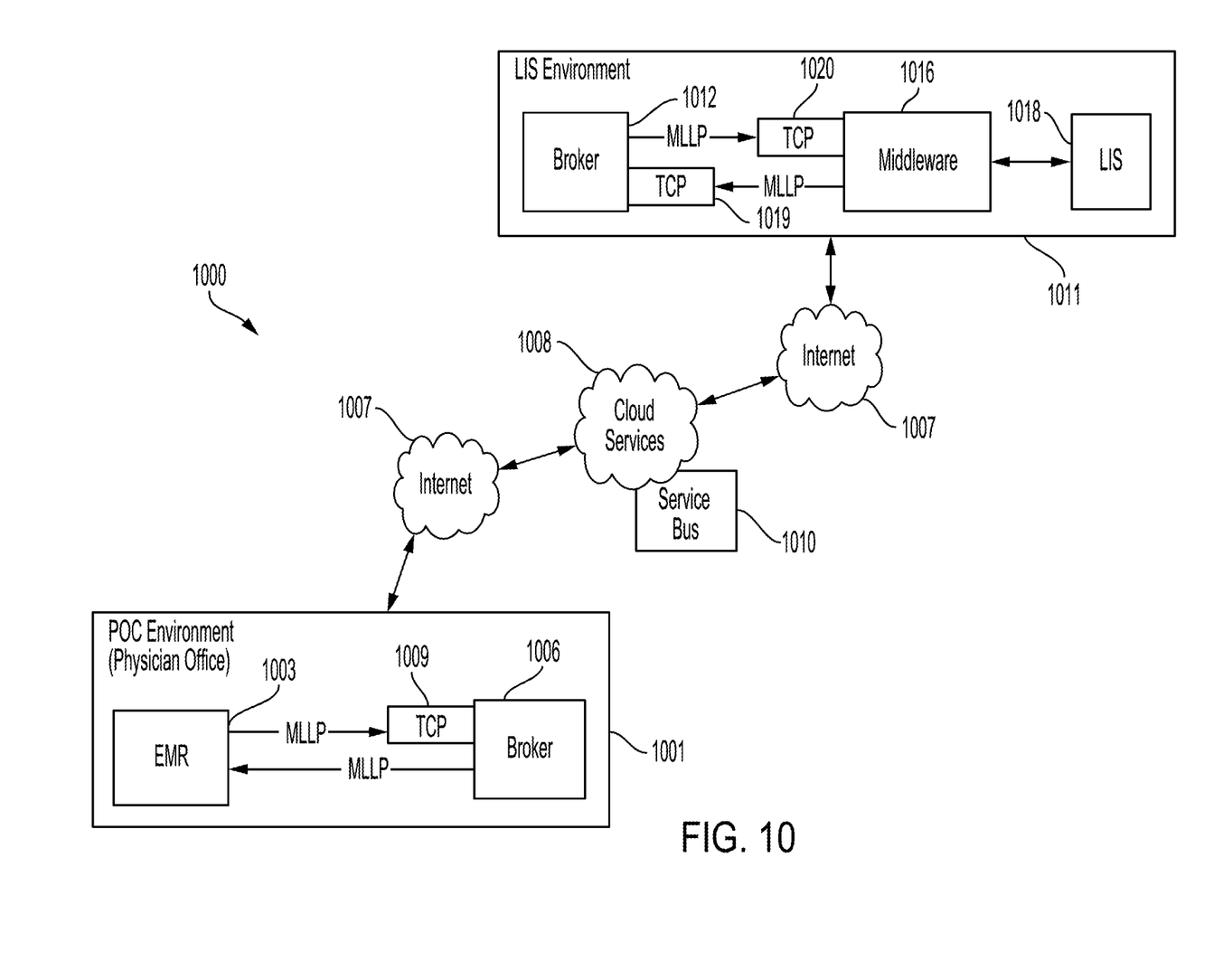
FIG. 10 is a block diagram depicting a system for providing a transparent secure link for point-of-care medical records according to aspects of the present disclosure.

FIG. 10 is a block diagram depicting a system for providing a transparent secure link for point-of-care medical records according to aspects of the present disclosure. System 1000 includes point-of-care (POC) environment 101, as an example, a physician office. POC environment 101 includes a computing device (not shown), which may be a mobile computing device as previously discussed. POC environment 1001 may also include one or more POCT devices as previously discussed. The computing device and local systems within POC environment may maintain patient EMRs, for example, EMR 1003. A local data broker 1006 may receive information from LIS environment 1011 over a wide-area network infrastructure as previously described and populate or update EMR 1003 with the information.

Local data broker 1006 can be a message oriented middleware software module to handle the flow of data between the POC EMR 1003 and service bus 1010 deployed in the cloud services platform 1008. Local data broker 1006 serves as an intermediary for the application that handles EMR 1003 and other applications to which the mobile computing device must interface over the wide-area network infrastructure. Service bus 1010 is used to decouple the applications with the POC environment 1001 from applications deployed in or behind the wide-area network infrastructure.

Still referring to FIG. 10, remote broker 1012 translates and/or encapsulates low-level EMR data received from LIS 1018 in LIS environment 1011 to provide secured EMR data to traverse the wide-area network infrastructure including the Internet 1007 without the need for an end-to-end encrypted channel such as might otherwise be provided by a VPN connection. Local data broker 1006 receives secured EMR data over the wide-area network infrastructure from remote broker 1012. In this example, remote broker 1012 handles the flow of data between centralized middleware 1016 and local data broker 1006. Remote broker 1012 receives low-level EMR protocol data, or at least information from the low-level EMR protocol data from middleware 1016, and encapsulates the low-level EMR data or information from the low-level EMR data in order to transmit the data to POC environment 1001 to update the healthcare information in POC EMR 1003. In this example, centralized middleware 116 provides a translation layer between LIS 1018 and remote broker 1012.

The LIS environment 1011 includes computer systems (not shown) within testing laboratories, hospitals, clinics, etc. that are connected to the LIS via LAN, virtual LAN, VPN, or are otherwise within the firewall or information security structure of the LIS. A device that is not connected to or related to the LIS in any of these ways can be said to be outside of or external to the LIS environment. Laboratories, hospitals, clinics, and the like are that are inside the LIS environment are typically affiliated or partnered in some way with the same entity that maintains the LIS. Remote data broker 1012 and centralized middleware 1016 may be part of the LIS environment, part of the wide-area network infrastructure, or components of either or both can reside in both.

Continuing with FIG. 10, as an example, messages within either or both of the LIS environment 1011 or the POC environment 1001 can be transmitted according to the Health Level 7 (HL7) standard, under which messages are exchanged using the ASCII-based minimal lower layer protocol (MLLP) as a low-level protocol for EMR data. Thus, in the context of system 1000, low-level EMR data can consist at least partly of MLLP messages. In the example of FIG. 10, such messages can be transmitted from middleware 1016, where they are received by a TCP listening stack 1019 for remote broker 1012. Similarly, MLLP messages can be transmitted from remote broker 1012 to TCP listening stack 1020 for middleware 1016. Remote broker 1012 encapsulates received low-level EMR data to securely transmit it to the POC environment 1001 over the wide-area network infrastructure.

Data broker 1006 can receive secured EMR data, access the low-level EMR data (MLLP) from the secured EMR data, and populate or update POC EMR 1003 using the EMR data, which may include new test results originally recorded by a POCT device either within POC environment 1001 or at another remote provider or clinic. In the event that information from the POC EMR needs to be sent back to the LIS, data broker 1006 includes a TCP listening stack 1009 to receive MLLP messages including data from POC EMR 1003.

Figure 11:
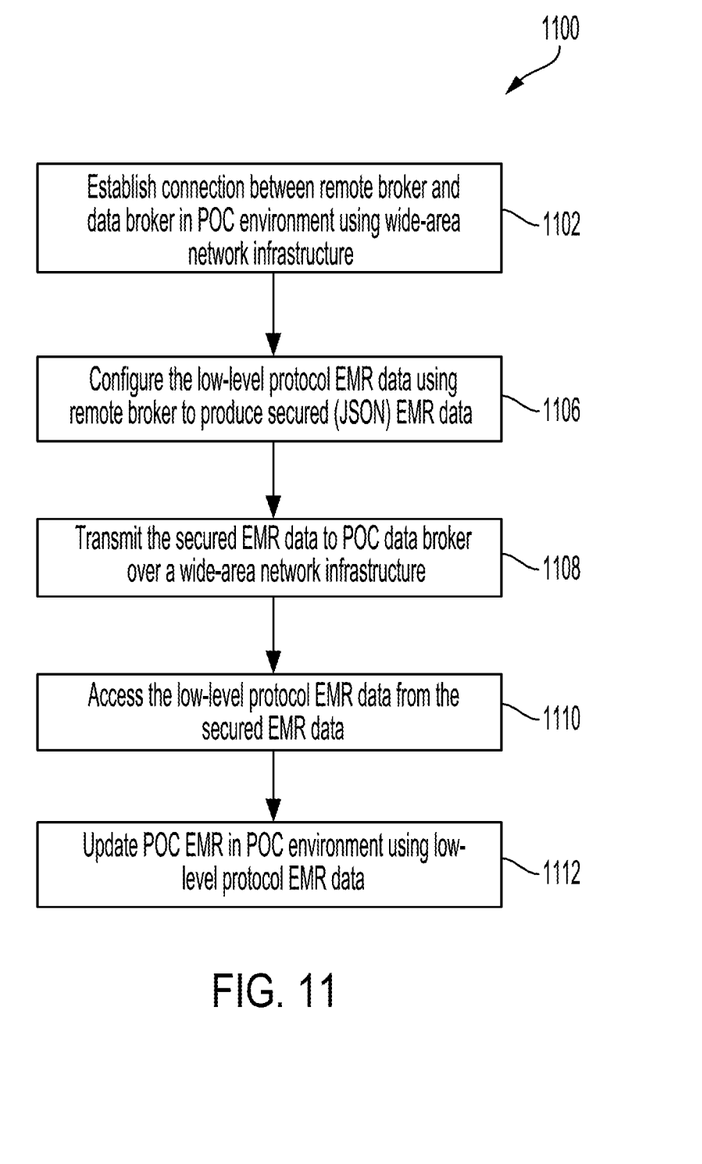
FIG. 11 is a flowchart illustrating a process of providing a transparent secure link for a point-of-care medical record according to aspects of the present disclosure.

FIG. 11 is a flowchart illustrating a process of providing a transparent secure link for a point-of-care medical record management according to aspects of the present disclosure. At block 1102, the processing devices within the POC environment and the LIS environment establish a connection between the local data broker 1006 and remote broker 1012. Data broker 1006 and the computing device running the data broker are outside the LIS environment. The real-time connection between the brokers in turn provides a connection between the POC EMR 1003 and the LIS 1018. At block 1106, a computing device, for example, a server running remote broker 1012 in the LIS environment, configures the low-level EMR data to produce secured EMR data for transit to POC environment 1001. As an example, the secured EMR data may include JSON messages encapsulating MLLP messages that further include EMR data. At block 1108, the secured POCT data is transmitted to the POC local data broker 1006 over a wide area network infrastructure that includes cloud services platform 1008. The cloud services platform 1008 can include service bus 1010, providing load-balancing, routing, and other functions using message queues. At block 1110, a computing device inside the POC environment 1001 running local data broker 1006 accesses the low-level EMR data from the secured EMR data, for example, by de-encapsulating the MLLP messages from the JSON messages. At block 1112, POC EMR 1003 is updated or populated with the low-level EMR data from the LIS.

Unless specifically stated otherwise, throughout this specification terms such as "processing," "computing," or the like refer to actions or processes of a computing or processing device, such as one or more computers or a similar electronic computing device or devices that manipulate or transform data represented as physical electronic or magnetic quantities within memories, registers, or other information storage devices, transmission devices, or display devices of the computing platform. The term "patient"

can refer to not only a human patient but also on animal on which POCT may be performed in a veterinary practice.

The system or systems discussed herein are not limited to any particular hardware architecture or configuration. A computing device can include any suitable arrangement of components that provides a result conditioned on one or more inputs. Suitable computing devices include multipurpose microprocessor-based computing systems accessing stored software that programs or configures the computing system from a general-purpose computing apparatus to a specialized computing apparatus implementing one or more aspects of the present subject matter. Any suitable programming, scripting, or other type of language or combinations of languages may be used to implement the teachings contained herein in software to be used in programming or configuring a computing device.

Aspects of the methods disclosed herein may be performed in the operation of such computing devices. The order of at some of the blocks presented in the examples above can be varied—for example, blocks can be re-ordered, combined, or broken into sub-blocks. Certain blocks or processes can be performed in parallel.

The use of "configured to" herein is meant as open and inclusive language that does not foreclose devices configured to perform additional tasks or steps. Additionally, the use of "based on" is meant to refer to actions or processes of a computing or processing device, and to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting. A "connection" between structures, systems, modules, networks or the like can refer to a direct connection or a connection through intervening structures, systems, modules, networks etc.

The foregoing description of the examples, including illustrated examples, of the subject matter has been presented only for the purpose of illustration and description and is not intended to be exhaustive or to limit the subject matter to the precise forms disclosed. Numerous modifications, adaptations, and uses thereof will be apparent to those skilled in the art without departing from the scope of this subject matter. The illustrative examples described above are given to introduce the reader to the general subject matter discussed here and are not intended to limit the scope of the disclosed concepts.

What is claimed is:

1. A system comprising:
   a non-transitory computer-readable medium including computer program code to provide a transparent secure link for point-of-care testing (POCT) devices; and
   a processor device communicatively coupled to the non-transitory computer-readable medium, wherein the processor device is configured for executing the computer program code to:
   establish, using a provider computing device, a connection between a provider POCT device and a data broker on the provider computing device;
   link, in response to the connection, the provider POCT device to a centralized laboratory information system (LIS) environment using the data broker and a remote broker associated with the centralized LIS environment, the remote broker residing in a wide-area network infrastructure decoupled from the provider computing device by a service bus;
   access, using the provider computing device during point-of-care testing with the provider POCT device, minimum lower layer protocol (MLLP) data from the provider POCT device;
   configure the MLLP data using the data broker on the provider computing device to produce secured POCT data;
   transmit, during the point-of-care testing, the secured POCT data to the centralized LIS environment;
   access, during the point-of-care testing, the MLLP data from the secured POCT data in the centralized LIS environment;
   populate, during the point-of-care testing, a centralized electronic medical record (EMR) in the centralized LIS environment using information from the MLLP data accessed from the secured POCT data using the remote broker; and
   configure both the centralized EMR for access in the centralized LIS environment and a point-of-care EMR for access at the provider computing device to enable simultaneous access to, at least, two different EMRs being updated in real time during the point-of-care testing.

2. The system of claim 1, wherein the processor device is configured for executing the computer program code to populate the centralized EMR in the centralized LIS environment by providing the information to centralized middleware configured to format the information for the centralized EMR.

3. The system of claim 1, wherein the data broker on the provider computing device is configured to encapsulate the MLLP data into JSON messages.

4. The system of claim 1, wherein the remote broker resides in at least one of the wide-area network infrastructure or the centralized LIS environment.

5. The system of claim 1, wherein the connection between the provider POCT device and the data broker on the provider computing device comprises TCP messages from the provider POCT device to the provider computing device.

6. A method comprising:
   establishing, using a provider computing device, a connection between a provider point-of-care-testing (POCT) device and a data broker on the provider computing device;
   linking, in response to the connection, the provider POCT device to a centralized laboratory information system (LIS) environment using the data broker and a remote broker associated with the centralized LIS environment, the remote broker residing in a wide-area network infrastructure decoupled from the provider computing device by a service bus;
   accessing, using the provider computing device during point-of-care testing with the provider POCT device, minimum lower layer protocol (MLLP) data from the provider POCT device;
   configuring the MLLP data using the data broker on the provider computing device to produce secured POCT data;
   transmitting, during the point-of-care testing, the secured POCT data to the centralized LIS environment;
   accessing, during the point-of-care testing, the MLLP data from the secured POCT data in the centralized LIS environment;
   populating, during the point-of-care testing, a centralized electronic medical record (EMR) in the centralized LIS environment using information from the MLLP data accessed from the secured POCT data using the remote broker; and configuring both the centralized EMR for access in the centralized LIS environment and a point-of-care EMR for access at the provider computing device to enable simultaneous access to, at least, two different EMRs being updated in real time during the point-of-care testing.

7. The method of claim 6, further comprising populating the centralized EMR in the centralized LIS environment by providing the information to centralized middleware configured to format the information for the centralized EMR.

8. The method of claim 6, wherein configuring the MLLP data further comprises encapsulating the MLLP data into JSON messages.

9. The method of claim 6, the remote broker resides in at least one of the wide-area network infrastructure or the centralized LIS environment.

10. The method of claim 6, wherein the connection between the provider POCT device and the data broker on the provider computing device comprises TCP messages from the provider POCT device to the provider computing device.

11. A non-transitory computer-readable medium including computer program code executable by a processor to cause a provider computing device to:

establish, using the provider computing device, a connection between a provider point-of-care-testing (POCT) device and a data broker on the provider computing device;

establish, using the data broker and in response to the connection, a link between the provider POCT device and a centralized laboratory information system (LIS) environment, through a remote broker residing in a wide-area network infrastructure decoupled from the provider computing device by a service bus;

receive, during point-of-care testing with the provider POCT device, minimum lower layer protocol (MLLP) data from the provider POCT device;

configure, during the point-of-care testing with the provider POCT device, the MLLP data using the data broker on the provider computing device to produce secured POCT data;

transmit, during the point-of-care testing with the provider POCT device, the secured POCT data to the centralized LIS environment using a wide-area network infrastructure, the secured POCT data configured to populate a centralized electronic medical record (EMR);

receive, during the point-of-care testing with the provider POCT device, from the centralized LIS environment, at least a portion of the centralized EMR; and configure both the centralized EMR for access in the centralized LIS environment and a point-of-care EMR for access at the provider computing device to enable simultaneous access to, at least, two different EMRs being updated in real time during the point-of-care testing.

12. The non-transitory computer-readable medium of claim 11, wherein the data broker on the provider computing device is configured to encapsulate the MLLP data into JSON messages.

13. The non-transitory computer-readable medium of claim 11, wherein the connection between the provider POCT device and the data broker on the provider computing device comprises TCP messages from the provider POCT device to the provider computing device.

14. The non-transitory computer-readable medium of claim 13, wherein the connection between the provider POCT device and the data broker comprises TCP messages from the provider POCT device to the provider computing device, and wherein the computer program code is executable by the processor to cause the provider computing device to:

receive user input; and open a TCP port to listen for a connection message from the provider POCT device in response to the user input.

15. A system comprising:

a non-transitory computer-readable medium including computer program code to provide a transparent secure link for point-of-care testing (POCT) devices to access a point-of-care (POC) electronic medical record (EMR) via a data broker on a provider computing device; and a processor device communicatively coupled to the non-transitory computer-readable medium, wherein the processor device is configured for executing the computer program code to:

access, during POC testing with a provider POCT device outside of a centralized laboratory information system (LIS) environment using minimum lower layer protocol (MLLP) data from the provider POCT device, a centralized EMR within the centralized LIS environment;

configure, during the POC testing with the provider POCT device, low-level EMR data from the centralized EMR using a remote broker to produce secured EMR data, wherein the remote broker resides in a wide-area network infrastructure decoupled from the provider computing device by a service bus;

transmit, during the POC testing with the provider POCT device, the secured EMR data to a plurality of POC locations including a POC environment where the provider POCT device resides;

access, during the POC testing with the provider POCT device, the low-level EMR data from the secured EMR data in the POC environment;

populate or update, during the POC testing with the provider POCT device and using information from the low-level EMR data, a POC EMR for access during the POC testing; and configure both the centralized EMR for access in the centralized LIS environment and the POC EMR for access at the provider computing device to enable simultaneous access to, at least, two different EMRs being updated in real time during the point-of-care testing.

16. The system of claim 15, wherein the remote broker is configured to encapsulate the low-level EMR data into JSON messages.

* * * * *